US010679738B2

(12) United States Patent
Ganesan et al.

(10) Patent No.: US 10,679,738 B2
(45) Date of Patent: Jun. 9, 2020

(54) IDENTIFICATION OF CODABLE SECTIONS IN MEDICAL DOCUMENTS

(71) Applicant: 3M INNOVATIVE PROPERTIES COMPANY, St. Paul, MN (US)

(72) Inventors: Kavita A. Ganesan, Salt Lake City, UT (US); Brian J. Stankiewicz, Mahtomedi, MN (US); David E. Yarowsky, Fulton, MD (US); Anna N. Rafferty, Burnsville, MN (US); Michael A. Nossal, Seattle, WA (US); Anthony R. Davis, Ashland, OR (US)

(73) Assignee: 3M Innovative Properties Company, Saint Paul, MN (US)

( * ) Notice: Subject to any disclaimer, the term of this patent is extended or adjusted under 35 U.S.C. 154(b) by 211 days.

(21) Appl. No.: 15/517,648

(22) PCT Filed: Oct. 20, 2015

(86) PCT No.: PCT/US2015/056300
§ 371 (c)(1),
(2) Date: Apr. 7, 2017

(87) PCT Pub. No.: WO2016/064775
PCT Pub. Date: Apr. 28, 2016

(65) Prior Publication Data
US 2017/0300635 A1 Oct. 19, 2017

Related U.S. Application Data

(60) Provisional application No. 62/065,930, filed on Oct. 20, 2014.

(51) Int. Cl.
*G06F 17/30* (2006.01)
*G16H 10/60* (2018.01)
(Continued)

(52) U.S. Cl.
CPC .............. *G16H 10/60* (2018.01); *G16H 15/00* (2018.01); *G06F 19/32* (2013.01); *G06F 19/321* (2013.01)

(58) Field of Classification Search
CPC .............. G06F 16/2453; G06F 16/9536; G06F 16/9538
See application file for complete search history.

(56) References Cited

U.S. PATENT DOCUMENTS 5,704,371 A * 1/1998 Shepard ................. G06Q 50/22
128/897
6,026,363 A * 2/2000 Shepard ................. G06Q 50/22
705/3
(Continued)

OTHER PUBLICATIONS

Pakhomov, "Automating the Assignment of Diagnosis Codes to Patient Encounters Using Example-based and Machine Learning Techniques", Journal of the American Medical Informatic Association, Oct. 2006, pp. 516-525.

(Continued)

*Primary Examiner* — Daniel A Kuddus
(74) *Attorney, Agent, or Firm* — 3M Innovative Properties Company; Jonathan V. Sry

(57) ABSTRACT

This disclosure describes systems, devices, and techniques for identifying sections of medical documents that are suitable for automated medical coding. In one example, a computer-implemented method includes receiving, by one or more processors, the medical document, wherein the medical document comprises a plurality of sections. The method also may include determining, by the one or more processors and via application of a classification model to each section of the plurality of sections, codability indicia for each section of the plurality of sections, wherein the codability indicia represents whether the respective section is suitable for automated medical coding. The method may
(Continued)

include outputting, by the one or more processors, the respective codability indicia for each section of the plurality of sections.

25 Claims, 7 Drawing Sheets

(51) Int. Cl.
    *G16H 15/00*     (2018.01)
    *G06F 19/00*     (2018.01)

(56) References Cited

U.S. PATENT DOCUMENTS

| | | |
|---|---|---|
| 6,915,254 B1 | 7/2005 | Heinze |
| 8,492,162 B2 * | 7/2013 | Kippenhan ............... A61L 2/24 |
| | | 436/164 |
| 2002/0198739 A1 * | 12/2002 | Lau ....................... G06F 19/324 |
| | | 705/3 |
| 2003/0105638 A1 | 6/2003 | Taira |
| 2004/0220895 A1 | 11/2004 | Carus et al. |
| 2008/0004505 A1 * | 1/2008 | Kapit ..................... G16H 15/00 |
| | | 600/300 |
| 2009/0313194 A1 * | 12/2009 | Amar ..................... G06F 16/353 |
| | | 706/20 |
| 2010/0000957 A1 | 1/2010 | Hutchinson |
| 2010/0036680 A1 * | 2/2010 | Familant ................. G06Q 10/10 |
| | | 705/3 |
| 2010/0306218 A1 * | 12/2010 | Bacon .................... G06F 19/324 |
| | | 707/759 |
| 2012/0043105 A1 | 2/2012 | Baird |
| 2013/0080187 A1 | 3/2013 | Bacon |
| 2013/0311207 A1 | 11/2013 | Kemp et al. |
| 2014/0108047 A1 * | 4/2014 | Kinney ................... G06Q 50/24 |
| | | 705/3 |
| 2014/0215301 A1 * | 7/2014 | Stone ..................... G16H 10/60 |
| | | 715/225 |
| 2014/0215391 A1 * | 7/2014 | Little .................... G06F 40/197 |
| | | 715/810 |
| 2014/0330587 A1 * | 11/2014 | Eisenhandler ......... G06Q 50/24 |
| | | 705/3 |

OTHER PUBLICATIONS

International Search Report for PCT International Application No. PCT/US2015/056300, dated Feb. 2, 2016, 2 pages.

* cited by examiner

IDENTIFICATION OF CODABLE SECTIONS IN MEDICAL DOCUMENTS

CROSS REFERENCE TO RELATED APPLICATIONS

This is a national stage filing under 35 U.S.C. 371 of PCT/US2015/056300, filed on Oct. 20, 2015, which claims priority to U.S. Provisional Application No. 62/065,930, filed on Oct. 20, 2014, the disclosure of which is incorporated by reference in its/their entirety herein.

TECHNICAL FIELD

The invention relates to systems and techniques for processing medical information contained in medical documents.

BACKGROUND

In the medical field, accurate processing of records relating to patient visits to hospitals and clinics ensures that the records contain reliable and up-to-date information for future reference. Accurate processing may also be useful for medical systems and professionals to receive prompt and precise reimbursements from insurers and other payors. Some medical systems may include electronic health record (EHR) technology that assists in ensuring records of patient visits and files are accurate in identifying information needed for reimbursement purposes. These EHR systems generally have multiple specific interfaces into which medical professionals across different healthcare facilities and settings may input information about the patients and their visits.

SUMMARY

In general, this disclosure describes systems and techniques for identifying sections of medical documents that are suitable for automated medical coding. For example, systems described herein may determine codability indicia for each section of a medical document. The respective codability indicia determined for each section may represent whether the section is suitable for automated medical coding. For example, codability indicia may represent that a section is suitable for automated medical coding or is not suitable for medical coding. The codability indicia may, in some examples, represent the types of medical information suitable for automated medical coding contained within each section. A system may select, based on the codability indicia determined for each section, sections of the medical document for automated medical coding.

In one example, this disclosure describes a computer-implemented method for processing a medical document, the method including receiving, by one or more processors, the medical document, wherein the medical document comprises a plurality of sections, determining, by the one or more processors and via application of a classification model to each section of the plurality of sections, codability indicia for each section of the plurality of sections, wherein the codability indicia represents whether the respective section is suitable for automated medical coding, and outputting, by the one or more processors the respective codability indicia for each section of the plurality of sections.

In another example, this disclosure describes a computerized system for processing a medical document, the system including a memory and one or more processors configured to receive the medical document and store the medical document in the memory, wherein the medical document comprises a plurality of sections, determine, via application of a classification model to each section of the plurality of sections, codability indicia for each section of the plurality of sections, wherein the codability indicia represents whether the respective section is suitable for automated medical coding, and output the respective codability indicia for each section of the plurality of sections.

In an additional example, this disclosure describes a computer-readable storage medium comprising instructions that, when executed, cause one or more processors to receive the medical document, wherein the medical document comprises a plurality of sections, determine, via application of a classification model to each section of the plurality of sections, codability indicia for each section of the plurality of sections, wherein the codability indicia represents whether the respective section is suitable for automated medical coding, and output the respective codability indicia for each section of the plurality of sections.

The details of one or more examples of the described systems, devices, and techniques are set forth in the accompanying drawings and the description below. Other features, objects, and advantages will be apparent from the description and drawings, and from the claims.

DETAILED DESCRIPTION

Figure 1:
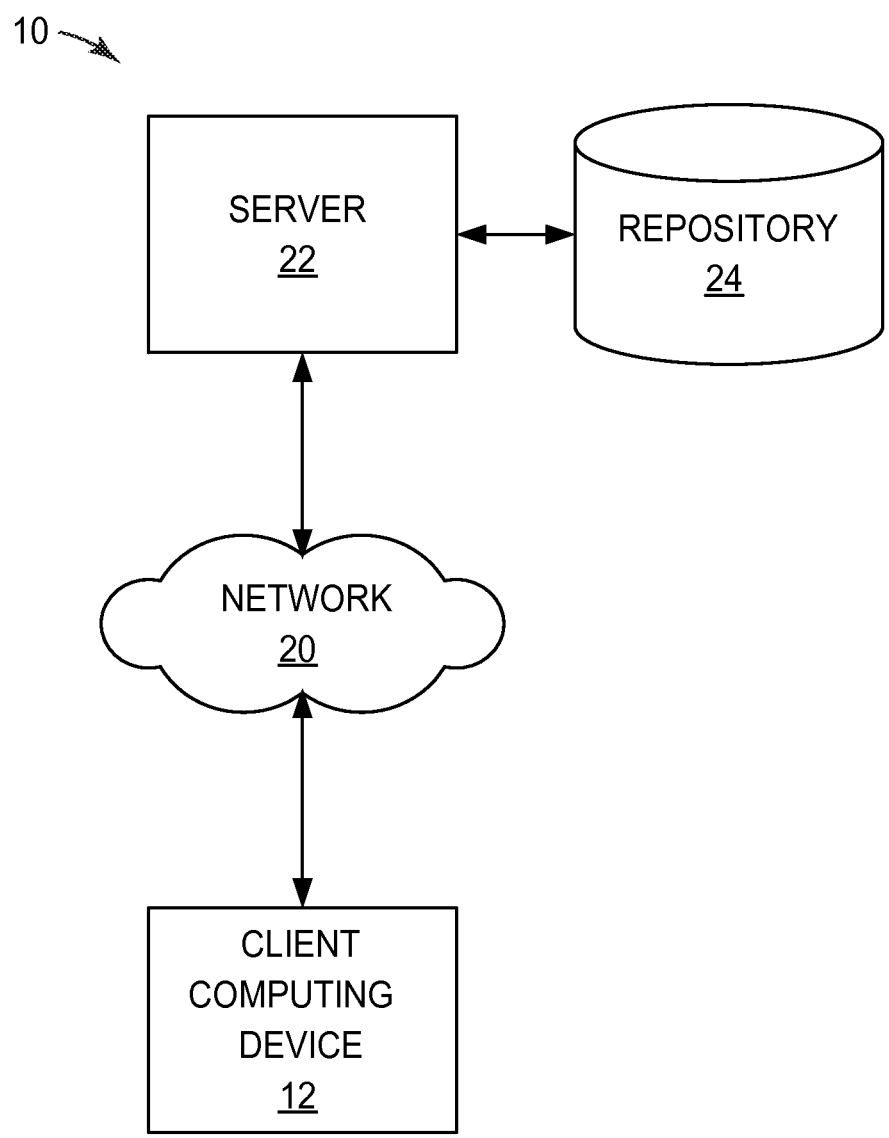
FIG. 1 is a block diagram illustrating an example distributed system configured to determine codability indicia for sections of medical documents consistent with this disclosure.

This disclosure describes systems and techniques for identifying sections of medical documents that are suitable for automated medical coding. When a physician visits with a patient (e.g., a patient encounter), the physician may perform various tasks such as evaluating the patient, reviewing medical history of the patient, determining the current medical condition of the patient, and performing a medical procedure on the patient. The physician (or other medical professional such as a physician's assistant or nurse) typically uses a computerized medical record system to enter information (e.g., into a medical document) documenting aspects of the patient encounter as medical information related to the patient. The information in the medical document is typically text in the form of a narrative that describes aspects of the patient encounter.

The information within the medical document may be organized into various sections of the medical document. Sections of the medical document may differ between different healthcare organizations, clinics, and physicians. For example, one healthcare organization may utilize three sections for respective types of medical information and another healthcare organization may utilize live sections for respective types of medical information. Therefore, the same types of medical information (e.g., historical information and diagnostic information) may be organized into different sections of different medical documents. In addition, different heading descriptions for each section, of the different medical documents may not accurately describe the types of information contained within each section.

For medical billing and/or medical document analysis, medical codes can be generated for each medical document. The medical codes are standardized abbreviations (e.g., alphanumeric codes) that represent content of the text within each medical document. Before a medical coding system can automatically code a medical document from a particular healthcare organization, the coding system may need to be configured to process the medical documents from the particular healthcare organization. One or more technicians (e.g., nosologists) may typically process sample medical documents from the healthcare organization to determine which of the sections are suitable for automatic medical coding and the types of information (e.g., historical, procedural, or diagnostic information) contained in sections corresponding to respective headers in the medical document. This process can be time consuming and inefficient. Manual analysis of sample medical documents may also result in inconsistent identification of the types of information in the sections of the medical documents and potentially erroneous medical coding of documents.

As described herein, a system may be configured to automatically determine codability indicia for sections of medical documents to identity which sections are suitable for automated medical coding and which sections are not suitable for automated medical coding. A system may first train a classification model that determines the codability indicia for sections of text. The system may receive training medical documents (e.g., sample documents) from a particular source (e.g., a healthcare organization) of the medical documents. The training medical documents may include sections already having annotations indicating which sections are codable, which sections are not codable, and/or which sections may or may not include certain types of information. The system may input the codable sections from these training medical documents to a statistical machine learning classifier, and the statistical machine learning classifier may analyze the text within annotated sections to determine what types of information are typically in each section of the training medical documents. The system then trains the classification model with the trained statistical machine learning classifier to determine codability indicia for sections for each type of medical document or each new medical document.

Once the classification model is trained, the system may apply the classification model to sections of text from medical documents to determine the codability indicia for each section. In some examples, the system may apply the classification model to different types of medical documents to determine codability indicia for each of the sections of each different type of medical documents. For example, the system may generate a configuration file that identifies, or assigns, the codability indicia for each section of the different types of medical documents. The system may generate codability indicia for each section of sample medical documents and set the codability indicia for each section of each type of medical document based on the typical codability indicia determined for each section. A system may use the configuration file to generate medical codes (or skip the automated medical coding process) for sections of newly received medical documents according to the configuration file. In some examples, the system may use the configuration file to determine which coding engines should be applied to each of the sections identified as suitable for medical coding. In other words, the system may use the configuration file to determine codability indicia typical for each section of new medical documents instead of applying the classification model to the text of each section.

In another example, a system may apply the trained classification model to newly received medical documents to predict which sections of the new medical documents should be processed for the automatic generation of medical codes. Prior to applying a coding engine to a new medical document, the system may apply the classification model to the medical document to determine codability indicia for one or more sections of the medical document. Based on the determined codability indicia for each section, the system may determine which one or more medical coding engines should be applied to each respective section. In this manner, the system may apply only those coding engines to the sections deemed applicable to the respective coding engines.

Sections that are identified as suitable for automated medical coding may thus be automatically coded by one or more medical coding engines. Conversely, sections that are identified as unsuitable for automated medical coding may be disregarded or excluded from the coding process to reduce processing of unnecessary portions of medical documents. As part of determining the codability indicia, a system may also identify one or more types of information contained within each section of a medical document suitable for medical coding. In other words, the system may determine codability indicia for each section of medical documents that indicate 1) if the section is suitable for medical coding, and 2) the type of coding engine appropriate for each section of the medical document. In this manner, medical coding throughput may be increased because the coding engines are only tasked with processing those sections identified has containing the type of information codable by the respective coding engine. In other words, coding engines are relieved from processing sections of text not likely to produce any medical codes from that particular coding engine. The system may also use the codability indicia to configure the medical coding process for medical documents from a particular healthcare organization. In this manner, the systems and processes described herein may improve the efficiency and quality of automated medical coding of medical documents.

FIG. 1 is a block diagram illustrating an example distributed system 10 configured to determine codability indicia for sections of medical documents consistent with this disclosure. As described herein, system 10 may include one or more client computing devices 12, a network 20, server computing device 22, and repository 24. Client computing device 12 may be configured to communicate with server 22 via network 20. Server 22 may receive various requests from client computing device 12 and retrieve various information from repository 24 to address the requests from client computing device 12. In some examples, server 22 may generate information, such as codability indicia for respective sections of medical documents or medical codes for sections of medical documents for client computing device 12. In some examples, server 22 may generate information, at the request of client computing device 12, solitarily or in parallel with the client computing device 12.

Server 22 may be and/or include one or more computing devices connected to client computing device 12 via network 20. Server 22 may perform the techniques described herein, and a user may interact with system 10 via client computing device 12. Network 20 may include a proprietary or non-proprietary network for packet-based communication. In one example, network 20 may include the Internet, in which case each of client computing device 12 and server 22 may include communication interfaces for communicating data according to transmission control protocol/internet protocol (TCP/IP), user datagram protocol (UDP), or the like. More generally, however, network 20 may include any type of communication network, and may support wired communication, wireless communication, fiber optic communication, satellite communication, or any type of techniques for transferring data between two or more computing devices (e.g., server 22 and client computing device 12).

Figure 2:
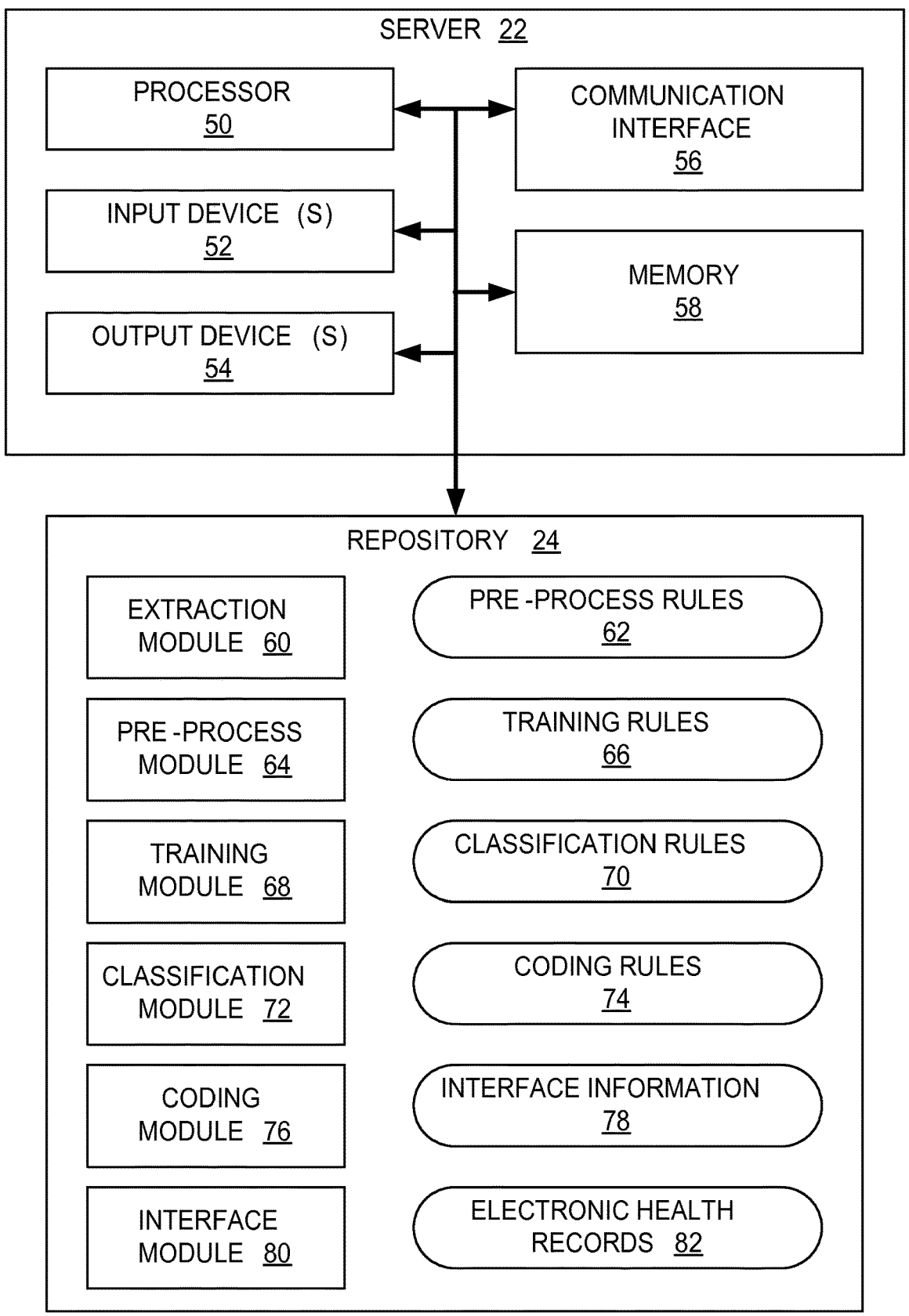
FIG. 2 is a block diagram illustrating the server and repository of the example distributed system of FIG. 1.

Server 22 may include one or more processors, storage devices, input and output devices, and communication interfaces, as described in FIG. 2. Server 22 may be configured to provide a service to one or more clients, such as determining codability indicia for sections of medical documents, generating configuration files for types of medical documents, and/or generating medical codes for medical documents. Server 22 may operate within a local network or be hosted in a Cloud computing environment. Client computing device 12 may be a computing device associated with a medical coding service (e.g., a company or service that generates medical codes for an entity) or an entity (e.g., a hospital, clinic, university, or other healthcare organization) that requests medical codes for medical documents generated by a physician during a patient encounter.

Figure 3:
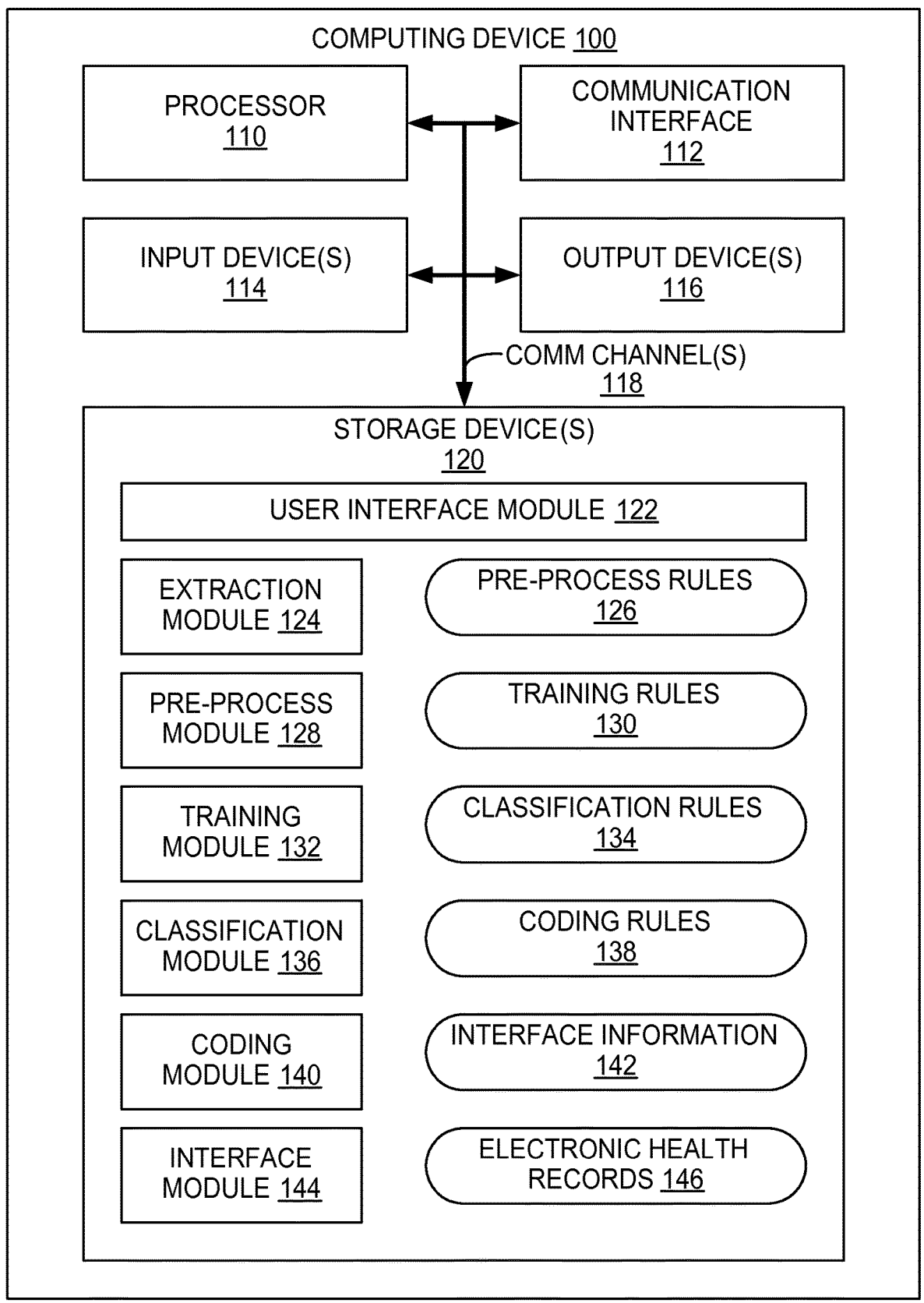
FIG. 3 is a block diagram illustrating a stand-alone computing device configured to determine codability indicia for sections of medical documents consistent with this disclosure.

Examples of client computing device 12 include personal computing devices, computers, servers, mobile devices, smart phones, and tablet computing devices. Client computing device 12 may be configured to communicate with server 22 and select training medical documents, request training of statistical machine learning classifiers, request training of classification models, request the generation of configuration files for types of medical documents, request automated medical coding, or otherwise interact with server 22 to perform the processes described herein. Alternatively, client computing device 12 may be configured to perform any of the processes described herein such as determining codability indicia for sections of medical documents and/or generate medical codes for codable sections of text without interaction or connection to server 22 as represented in FIG. 3. Server 22 may also be configured to communicate with multiple client computing devices 12 associated with the medical coding service and/or with an entity utilizing the medical coding service.

Server 22 may be configured to train a classification model with training medical documents and determine codability indicia for sections of medical documents with the trained classification model. Server 22 may additionally, or alternatively, be configured to generate medical codes representing at least some of information contained within medical documents. Server 22 is described as performing the techniques described herein, and client computing device 12 may receive user input requesting that server 22 perform one or more processes, receiver user input managing or correcting the determination of codability indicia, present determined codability indicia for sections of medical documents, and/or present medical codes generated by server 22 for medical documents based on the codability indicia for the medical documents. However, in other examples, client computing device 12 may perform one or more processes attributed to server 22. Moreover, server 22 and client computing device 12 may operate as a distributed system that is configured to perform one or more processes related to determining codability indicia and/or generating medical codes.

Server 22 may process medical documents to determine whether or not the medical documents, or one or more sections of text therein, are suitable for automated medical coding. In one example, server 22 may include one or more processors or modules configured to receive a medical document that includes one or more sections of text. Server 22 may then determine, via application of a classification model to each section of the medical document, codability indicia for each section. In some examples, server 22 may apply the classification model to each of the sections of the medical document. The codability indicia represents whether the respective section is suitable for automated medical coding, and, in some examples, the codability indicia may represent what types of information related to medical coding are contained within the respective section. Server 22 may then output the respective codability indicia for each section of the medical document. Server 22 may store the determined codability indicia in memory, output the codability indicia for presentation to a user, and/or output the codability indicia to another computing device. In other words, the determined codability indicia may be presented to a user or utilized to facilitate additional analysis on the medical document or other medical documents.

A section of text may be suitable for automated medical coding when the text includes information relevant to medical coding. For example, a section of text that includes information that would produce one or more medical codes would be considered relevant to medical coding. In the example of International Classification of Diseases (ICD)-9 or ICD-10 medical codes, a section may be codable if the section has language (e.g., text) that is fit for generating one or more codes from the ICD-9 or ICD-10 codeset. In contrast, a section may not be suitable for automated medical coding when the section does not include any information that would produce at least one medical code during coding process. In some examples, a section may be determined to be suitable for automated medical coding when the section typically would include information that produces a medical code, even if the actual section does not include any information that would produce a medical code. For example, the section may be associated with a header describing medical procedures, which may typically include information that produces procedural codes, but the actual section that is processed may not include any relevant information because no procedures were performed during that particular patient encounter. Server 22 may determine codability indicia for medical documents that have not yet been subjected to automated medical coding prior to the determination. In other words, server 22 may determine codability indicia for uncoded medical documents. In some examples, the medical documents may have already been coded for one type of medical information and not yet coded for medical information related to the codability indicia.

Server 22 may be configured to receive medical documents and/or pre-processed portions of medical documents. Server 22 may receive medical documents from client computing device 12 (e.g., an upload of one or more medical documents from an entity such as a clinic or healthcare organization) or repository 24 if the medical documents have already been stored in repository 24. In some examples, the medical documents may be stored as part of one or more electronic health records (EHR) of patients or separate from any EHR. Server 22 may receive one medical document at a time or receive batches of medical documents at a given time for the determination of codability indicia or generation of medical codes described herein. In some examples, one or more processors of server 22 may receive the medical documents from another module (e.g., an input device or communication interface) within server 22 that received the medical documents from a different computing device.

A section of a medical document may be a portion of the text contained within the medical document. A medical document may include only one section of text or two or more sections of text. Different sections of a medical document may be separated by one or more formatting breaks (e.g., headings, page breaks, paragraph breaks, or certain punctuation), words or phrases, specified characters, or other marker in the text. Server 22 may receive medical documents already separated into different sections. In other examples, server 22 may pre-process the medical documents to obtain each section. For example, server 22 may be configured to identity each of the one or more sections in a medical document and extract the sections for individual analysis by the classification model (e.g., determination of codability indicia). Server 22 may identify each section in the medical document by separating portions of text within the medical document according to one or more formatting breaks located within the text. The formatting breaks may include one or more headers located within the text, where each of the one or more headers corresponds to a respective section in the medical document. In other words, each header in the medical document may indicate that a respective section of text associated with the header follows the header in the text. Medical documents of the same type may include similar headers that identify similar types of information between medical documents.

Prior to determining codability indicia for medical documents, a classification model may be developed in order to accurately predict the codability indicia for medical documents. For example, server 22 may receive a plurality of training medical documents. The training medical documents may be sample medical documents representative of new medical documents to be received and processed in the future from the entity (e.g., a healthcare organization). Each training medical document may include annotations indicating respective sections of the training medical document suitable for automated medical coding. For example, the annotations may indicate sections of text related to one or more type of medical information. In other words, the annotations may indicate which sections of the medical document are positive examples of text suitable for coding and which section of the medical document are negative examples of text suitable for coding. The annotations may be manually generated or reviewed by a coding expert, document specialist, nosologist, or some other technician.

Server 22 may then train a statistical machine learning classifier with the plurality of training medical documents. For example, server 22 may input the training medical documents that contain respective annotations to the statistical machine learning classifier. An example statistical machine learning classifier may include a Naïve Báyes classifier, but other classifiers may be used in other examples. The trained statistical machine learning classifier may then be used by server 22 to generate a classification model to determine codability indicia for sections of medical documents. In this manner, server 22 may determine the codability indicia for sections of medical documents by applying the trained classification model to each section of a medical document to determine the codability indicia for each section.

As described herein, server 22 may be configured to determine codability indicia for each section of a medical document by determining that at least one section of the medical document is not suitable for automated medical coding. In other words, server 22 may exclude one or more sections of a medical document from those sections to be medically coded. In addition, or alternatively, server 22 may determine codability indicia for each section by determining that at least one section of the medical document is suitable for automated medical coding. In some examples, determining codability indicia may include determining the types of medical information included within codable sections. Server 22 may identify one or more types of medical information contained within a codable section, where the one or more types of medical information are selected from a plurality of types of medical information.

Each type of medical information of the plurality of types of medical information may be associated with a respective codability indicium. The types of medical information may correspond to respective medical coding engines configured to generate medical codes from text within medical documents. In other words, the codability indicia may specify which coding engines are applicable to a specific section of the medical document. Server 22 may then assign, to each section, the one or more codability indicium for the respective types of medical information identified as contained within the respective section. In this manner, the codability indicia determined for each section may include one or more different codability indicium for the respective types of medical information.

Example types of medical information may include history information, procedural information, diagnostic information, and evaluation management information. The codability indicia may include an indication of whether the section is suitable for each type of a plurality of types of automated medical coding including, but limited to, a binary indication (e.g., true or false) of whether the section is suitable for each type of a plurality of types automated medical coding, a probability that the section is suitable for automated medical coding, a percentage indicative of whether the section is suitable for automated medical coding, and respective colors selected from a plurality of colors that indicate whether the section is suitable for automated medical coding. In this manner, codability indicia may be any textual, numerical, or graphical indication of the types of medical information contained within a section of text. In some examples, the codability indicia may include a level of confidence for each section that the determined codability indicia are accurate. Server 22 may generate a flag for any section that has a level of confidence below a predetermined acceptability threshold. The flag may indicate that a nosologist or other technician should review the section and the determined codability indicia to ensure that the section is codable and what types of information is included within the section.

In some examples, server 22 may generate a configuration file for each type of medical document that indicates the codability indicia for typical sections of the types of medical documents. For each section, the configuration file may indicate the type of medical document, the sections that were extracted, the header name for each section, example text from the section, and which type of medical information was contained within the section. Each type of medical information may be associated with a different medical coding engine. In some examples, an indication that types of medical information were not identified within the section may be used to represent that the section is not suitable for automated medical coding. Server 22 may store the configuration file in repository 24, transmit the configuration file to one or more other computing devices that execute the medical coding engines, and/or output the configuration file for display (e.g., presentation by an output device of client computing device 12). Server 22 may also output the codability indicia. As examples, server 22 may output the codability indicia as a file or instructions to another computing device that generates medical codes for medical documents, store the codability indicia in repository 24, and/or output, for display to a user, the codability indicia. In some examples, server 22 or client computing device 12 may present, on a display, the determined codability indicia for one or more sections of medical documents. In some examples, a processor of server 22 and/or client computing device 12 may be configured to control a display device to present the codability indicia for the one or more sections of the medical document.

Server 22 may, in some examples, generate medical codes for medical documents based on the determined codability indicia. In one example, server 22 may generate medical codes for the same sections for which the codability indicia were determined. Server 22 may select, based on the determined codability indicia, one or more sections suitable for automated medical coding, generate, via application of a medical coding engine to each of the selected codable sections, one or more medical codes, and output the one or more medical codes for the selected sections. Server 22 may apply the same coding engine for each of the sections suitable for medical coding. Alternatively, server 22 may apply one or more coding engines of a plurality of coding engines to respective sections. For example, if the determined codability indicia indicate that a section contains information associated with two different coding engines, server 22 may apply both of the coding engines to the text of the section. In this manner, server 22 may apply the appropriate one or more coding engines to each section determined to be suitable for automated medical coding. In another example, server 22 may use a generated configuration file to identify sections of a new medical document that are typically suitable for medical coding and apply the appropriate coding engines to the respective sections of the new medical document. In this manner, server 22 may not need to determine codability indicia for sections of new medical documents once the configuration file has been generated for those same types of medical documents.

The processes described with respect to FIG. 1 and herein may be performed by one or more servers 22. In other examples, client computing device 12 may perform one or more of the steps of processes such as determining codability indicia or generating medical codes. In this manner, system 10 may be referred to as a distributed system in some examples. Server 22 may utilize additional processing resources by transmitting some or all of the medical documents to additional computing devices.

Client computing device 12 may be used by a user (e.g., a medical professional such as physician, a healthcare facility administrator, a governmental regulatory agency, or a medical coding expert) to request determination of codability indicia, request the generation of medical codes, review codability indicia, review configuration files, or interact with server 22 in any other manner. Client computing device 12 may include one or more processors, memories, input and output devices, communication interfaces for interfacing with network 20, and any other components that may facilitate the processes described herein. In some examples, client computing device 12 may be similar to computing device 100 of FIG. 3. In this manner, client computing device 12 may be configured to perform one or more processes such as training a statistical machine learning classifier, generating a classification model, determining codability indicia, or generating medical codes with the aid of server 22, in some examples.

FIG. 2 is a block diagram illustrating the server and repository of the example system 10 of FIG. 1. As shown in FIG. 2, server 22 includes processor 50, one or more input devices 52, one or more output devices 54, communication interface 56, and memory 58. Server 22 may be a computing device configured to perform various tasks and interface with other devices, such as repository 24 and client computing devices (e.g., client computing device 12 of FIG. 1). Although repository 24 is shown external to server 22, server 22 may include repository 24 within a server housing in other examples. Server 22 may also include other components and modules related to the processes described herein and/or other processes. The illustrated components are shown as one example, but other examples may be consistent with various aspects described herein.

Processor 50 may include one or more general-purpose microprocessors, specially designed processors, application specific integrated circuits (ASIC), field programmable gate arrays (FPGA), a collection of discrete logic, and/or any type of processing device capable of executing the techniques described herein. In some examples, processor 50 or any other processors herein may be described as a computing device. In one example, memory 58 may be configured to store program instructions (e.g., software instructions) that are executed by processor 50 to carry out the processes described herein. Processor 50 may also be configured to execute instructions stored by repository 24. Both memory 58 and repository 24 may be one or more storage devices. In other examples, the techniques described herein may be executed by specifically programmed circuitry of processor 50. Processor 50 may thus be configured to execute the techniques described herein. Processor 50, or any other processors herein, may include one or more processors.

Memory 58 may be configured to store information within server 22 during operation. Memory 58 may comprise a computer-readable storage medium. In some examples, memory 58 is a temporary memory, meaning that a primary purpose of memory 58 is not long-term storage. Memory 58, in some examples, may comprise a volatile memory, meaning that memory 58 does not maintain stored contents when the computer is turned off. Examples of volatile memories include random access memories (RAM), dynamic random access memories (DRAM), static random access memories (SRAM), and other forms of volatile memories known in the art. In some examples, memory 58 is used to store program instructions for execution by processor 50. Memory 58, in one example, is used by software or applications running on server 22 (e.g., one or more of modules 60, 64, 68, 72, 76, and 80) to temporarily store information during program execution.

Input devices 52 may include one or more devices configured to accept user input and transform the user input into one or more electronic signals indicative of the received input. For example, input devices 52 may include one or more presence-sensitive devices (e.g., as part of a presence-sensitive screen), keypads, keyboards, pointing devices, joysticks, buttons, keys, motion detection sensors, cameras, microphones, or any other such devices. Input devices 52 may allow the user to provide input via a user interface.

Output devices 54 may include one or more devices configured to output information to a user or other device. For example, output device 54 may include a display screen for presenting visual information to a user that may or may not be a part of a presence-sensitive display. In other examples, output device 54 may include one or more different types of devices for presenting information to a user. Output devices 54 may include any number of visual (e.g., display devices, lights, etc.), audible (e.g., one or more speakers), and/or tactile feedback devices. In some examples, output devices 54 may represent both a display screen (e.g., a liquid crystal display or light emitting diode display) and a printer (e.g., a printing device or module for outputting instructions to a printing device). Processor 50 may present a user interface via one or more of input devices 52 and output devices 54, whereas a user may control the generation and analysis of medical documents via the user interface. In some examples, the user interface generated and provided by server 22 may be output for display by a client computing device (e.g., client computing device 12).

Server 22 may utilize communication interface 56 to communicate with external devices via one or more networks, such as network 20 in FIG. 1, or other storage devices such as additional repositories over a network or direct connection. Communication interface 56 may be a network interface card, such as an Ethernet card, an optical transceiver, a radio frequency transceiver, or any other type of device that can send and receive information. Other examples of such communication interfaces may include Bluetooth, 3G, 4G, and WiFi radios in mobile computing devices as well as USB. In some examples, server 22 utilizes communication interface 56 to wirelessly communicate with external devices (e.g., client computing device 12) such as a mobile computing device, mobile phone, workstation, server, or other networked computing device. As described herein, communication interface 36 may be configured to receive medical documents, instructions from a user, and/or transmit determined codability indicia, configuration files, and/or generated medical codes over network 20 as instructed by processor 50.

Repository 24 may include one or more memories, repositories, databases, hard disks or other permanent storage, or any other data storage devices. Repository 24 may be included in, or described as, cloud storage. In other words, information stored in repository 24 and/or instructions that embody the techniques described herein may be stored in one or more locations in the cloud (e.g., one or more repositories 24). Server 22 may access the cloud and retrieve or transmit data as requested by an authorized user, such as client computing device 12. In some examples, repository 24 may include Relational Database Management System (RDBMS) software. In one example, repository 24 may be a relational database and accessed using a Structured Query Language (SQL) interface that is well known in the art. Repository 24 may alternatively be stored on a separate networked computing device and accessed by server 22 through a network interface or system bus, as shown in the example of FIG. 2. Repository 24 may in other examples be an Object Database Management System (ODBMS), Online Analytical Processing (OLAP) database or other suitable data management system.

Repository 24 may store instructions and/or modules that may be used to perform the techniques described herein related to generating classification models, determining codability indicia for sections of medical documents, generating configuration files for types of medical documents, and generating medical codes for medical documents. As shown in the example of FIG. 2, repository 24 includes extraction module 60, pre-process module 64, training module 68, classification module 72, coding module 76, and interface module 80. Processor 50 may execute each of modules 60, 64, 68, 72, 76, and 80 as needed to perform various tasks. Repository 24 may also include additional data such as information related to the function of each module and server 22. For example, repository 24 may include pre-process rules 62, training rules 66, classification rules 70, coding rules 74, interface information 78, and electronic health records 82. Repository 24 may also include additional data related to the processes described herein. In other examples, memory 58 or a different storage device of server 22 may store one or more of the modules or information stored in repository 24. In some examples, one or more of modules 60, 64, 68, 72, 76, and 80 and/or associated instructions may be stored in a different memory such as memory 58 of server 22, a remote storage device, or a memory of another computing device.

As described herein, server 22 may receive medical information entered (e.g., created) by a physician or at the direction of a physician to represent an encounter with a patient. For example, processor 50 may receive one or more medical documents describing the patient encounter or including notes regarding the patient. These medical documents may be stored in Electronic Health Records (EHR) 82. EHR 82 may include medical documents for a single patient or medical documents for a plurality of respective patients. EHR 82 may include training medical documents for generating classification models and/or medical documents for which codability indicia may be determined prior to being coded by one or more medical coding engines.

Processor 50 may be configured to generate a classification model that can determine codability indicia for sections of medical documents received from an entity (e.g., a healthcare organization). Processor 50 may receive training medical documents from the entity and/or receive the training medical documents already stored in EHR 82. Extraction module 60 may first identify and extract the sections from each of the training medical documents. For example, extraction module 60 may extract sections based on formatting breaks in the text of each medical document, such as headings location within the medical documents. In some examples, extraction module 60 may extract sections according to breaks identified by annotations for the respective training medical documents.

Pre-process module 64 may then perform pre-processing on each of the extracted sections of the training medical documents according to the instructions stored in pre-process rules 62. For example, pre-process rules 62 may cause pre-processing module 64 to remove stop words (e.g., prepositions and connector words such as he, is, at, which, and on) remove words that occur less than a predetermined number of times within the section (e.g., less than two times or less than three times), and/or ignore any lines less than a predetermined number of characters long (e.g., less than 5 characters or less than 10 characters). These modifications to the sections of text may aid in the natural language processing used to generate the classification model. In addition pre-process module 64 may mask all numbers in the text of each section into hash tags or other anonymous characters or symbols. This masking of numbers may promote patient privacy.

Training module 68 may generate a classification model based on the pre-processed sections of the training medical documents according to the instructions in training rules 66. For example, training module 68 may be configured to train a statistical machine learning classifier with the pre-processed sections of the training medical documents. Annotations associated with the sections may direct the statistical machine learning classifier to identify natural language associated with various types of medical information that is suitable for automated medical coding. An example statistical machine learning classifier may be a Naïve Bayes classifier, but a different probabilistic classifier may be used in other examples. In some examples training module 68 may include a natural language processing (NLP) engine that can process one or more of the training medical documents and select a statistical machine learning classifier most appropriate for the information contained in the training medical documents. The training medical documents may be of different types of medical documents. Training module 68 may select different statistical machine learning classifiers for respective different types of medical documents.

Training module 68 may also generate a classification model with the statistical machine learning classifier and according to the instructions in training rules 66. The classification model may thus define how sections of medical documents are determined to be suitable for automated medical coding. For example, the classification model may be stored in classification rules 70 and used by classification module 72 to determine codability indicia for sections of medical documents. In some examples, training module 68 may continue to update the classification based on newly processed medical documents and/or manual corrects to the codability indicia received from users.

Classification module 72 may determine codability indicia for sections of medical documents according to classification rules 70 (e.g., a classification model generated by training module 68). Classification module 72 may apply the generated classification model to the sections of the medical document to determine codability indicia for each of the sections. Classification module 72 may apply the classification model to sample medical documents from an entity to generate a classification file indicating which sections for each type of medical document are suitable for automatic medical coding and, in some examples, the types of medical information contained within each section to facilitate the selection of the appropriate coding engines for each section. In this manner, server 22 or another computing device may perform automated medical coding on new medical documents according to identified sections of the medical documents without requiring classification module 72 to process each section of every medical document prior to coding. However, as described below, classification module 72 may be implemented to determine codability indicia for every section prior to automated medical coding.

The codability indicia may represent whether the section is suitable for automated medical coding. Codability indicia for sections suitable for automated medical coding may also represent what types of medical information is contained within the codable section. For example, the codability indicia may represent whether or not the section includes types of medical information such as diagnosis information, procedural information, or historical information. Each of these types of medical information may be associated with a different type of medical coding engine. Therefore, codability indicia representing that a section includes one or more of these types of medical information also indicates which respective types of coding engines should be applied to the section. A section in which the codability indicia are negative for all types of medical information associated with medical coding may thus be identified as a section not suitable for automated medical coding.

As described herein, classification module 72 may be utilized for different purposes. In one example, classification module 72 may be used to generate a configuration file characterizing how the sections of one or more types of medical documents for an entity should be coded by coding module 76. In other words, classification module 72 may be applied to sample medical documents from the entity to determine codability indicia for each of the sections within each type of medical document to be coded. The configuration file may then identify, for each type of medical document, which section is suitable for medical coding and, if suitable for medical coding, what type or types of coding engines are appropriate for generating medical codes for the respective section. Once the configuration file is complete, server 22 may identify the sections within new medical documents and only code those sections identified by the configuration file as suitable for medical coding with the specified one or more medical coding engines. Classification module 72 may generate the configuration file using a set of sample medical documents from the entity and set the codability indicia in the configuration file to the most frequent codability indicia determined for each section of the sample medical documents.

In another example, classification module 72 may process the sections of each new medical document that needs to be coded or those new medical documents that have sections that do not align with a generated configuration file. In this manner, classification module 72 may operate as a filter in which classification module 72 applies the classification model to the sections of the new medical document to determine codability indicia and filter out any sections not suitable for medical coding. The codability indicia determined for each section by classification module 72 may also be used by processor 50 to transfer the codable sections of text to only those medical coding engines according to the codability indicia. In other words, the codability indicia may identify the coding engines appropriate for the information contained within each section suitable for automated medical coding.

Before determining codability indicia for sections of medical documents, server 22 may utilize extraction module 60 to extract sections of text from the medical documents. In some examples, preprocess module 68 may also perform similar pre-processing tasks on the extracted sections of medical documents to aid classification module 72 and mask private data of the patient. In this manner, processor 50 may execute extraction module 60 and/or pre-process module 64 for those medical documents used to generate a configuration file or those medical documents processed for medical codes.

According to the configuration file for medical documents and/or the determined codability indicia, coding module 76 may generate medical codes representing the information contained within each section suitable for automated medical coding. Classification module 72 may transfer those sections of text determined to be suitable for automated medical coding to coding module 76. In some examples, classification module 72 may specify which coding engines of coding module 76 should be applied to each section based on the codability indicia and/or the configuration file.

Coding rules 74 may include instructions that define the operation of coding module 76. For example, coding rules 74 may define the operation of one or more coding engines applied by coding module 76. Each coding engine may be specific to a particular medical codeset (e.g., IDC-9 or ICD-10 codesets) and/or specific to a particular type of medical information. For example, coding module 76 may be configured to operate a diagnosis coding engine, a procedural coding engine, a historical coding engine, and an evaluation management coding engine. Each of these coding engines may correspond to the types of information contained within a section of text as identified by the codability indicia. Although coding module 76 may operate different coding engines, separate coding modules may operate respective coding engines in other examples. Coding module 76 may output the medical codes generated for each of the processed sections of text.

Interface module 80 may output any of the information generated by modules 60, 64, 68, 72, and 76. For example, interface module 80 may output the configuration file generated by classification module 72 to another computing device for use in coding other medical documents or for display at a computing device (e.g., client computing device 12). Interface module 80 may also output the determined codability indicia for sections of medical documents to other computing devices and/or for display on a display device. In addition, interface module 80 may be configured to output generated medical codes to other computing devices or for display. Interface module 80 may also be configured to receive information from other computing devices, such as training medical documents or other medical documents to be processed. Interface information 78 may include instruction that define the operation of interface module 80. Interface module 80 may also receive user input requesting various modules to perform the functions described herein.

FIG. 3 is a block diagram illustrating stand-alone computing device 100 configured to determine codability indicia for sections of medical documents consistent with this disclosure. Computing device 100 may be substantially similar to server 22 and repository 24 of FIG. 2. However, computing device 100 may be a stand-alone computing device configured to determine codability indicia and/or generate medical codes for medical documents. Computing device 100 may be configured as a workstation, desktop computing device, notebook computer, tablet computer, mobile computing device, or any other suitable computing device or collection of computing devices.

As shown in FIG. 3, computing device 100 may include processor 110, one or more input devices 114, one or more output devices 116, communication interface 112, and one or more storage devices 120, similar to the components of server computing device 22 of FIG. 2. Computing device 100 may also include communication channels 118 (e.g., a system bus) that allows data flow between two or more components of computing device 100, such as between processor 110 and storage devices 120. Computing device 100 also includes one or more storage devices 120, such as a memory, that stores information such as instructions for performing the processes described herein and data such as medical documents for a patient and algorithms for generating a classification model, generating a configuration file, determining codability indicia and/or generating medical codes.

Storage devices 120 may include data for one or more modules and information related to the codability indicia and automatic medical coding described herein. For example, storage devices 120 may include extraction module 124, pre-process module 128, training module 132, classification module 136, coding module 140, and interface module 144, similar to the modules described with respect to repository 24 of FIG. 2. Storage devices 120 may also include, information such as pre-processing rules 126, training rules 130, classification rules 134, coding rules 138, interface information 142, and Electronic Health Records (EHR) 146, similar to the information described as stored in repository 24.

The information and modules of storage devices 120 of computing device 100 may be specific to a healthcare entity that employs computing device 100 to determine codability indicia and generate medical codes for medical documents. For example, classification module 136 may determine codability indicia for sections of medical documents that facilitate automated medical coding by coding module 140. Alternative the information and modules of storage devices 120 of computing device 10 may be specific to a medical document processing service that generates configuration files for the types of medical documents from an entity and generates medical codes based on the configuration files. In any case, computing device 100 may be configured to perform any of the processes and tasks described herein and with respect to server 22 and repository 24. Storage devices 120 may also include user interface module 144, which may provide a user interface for a user via input devices 114 and output devices 116.

In some examples, input devices 114 may include one or more scanners or other devices configured to convert paper documents into electronic clinical documents that can be processed by computing device 100. In other examples, communication interface 112 may receive electronic clinical documents from a repository or individual clinician device on which clinical documentation are initially generated. Communication interlace 112 may thus send and receive information via a private or public network.

Figure 4:
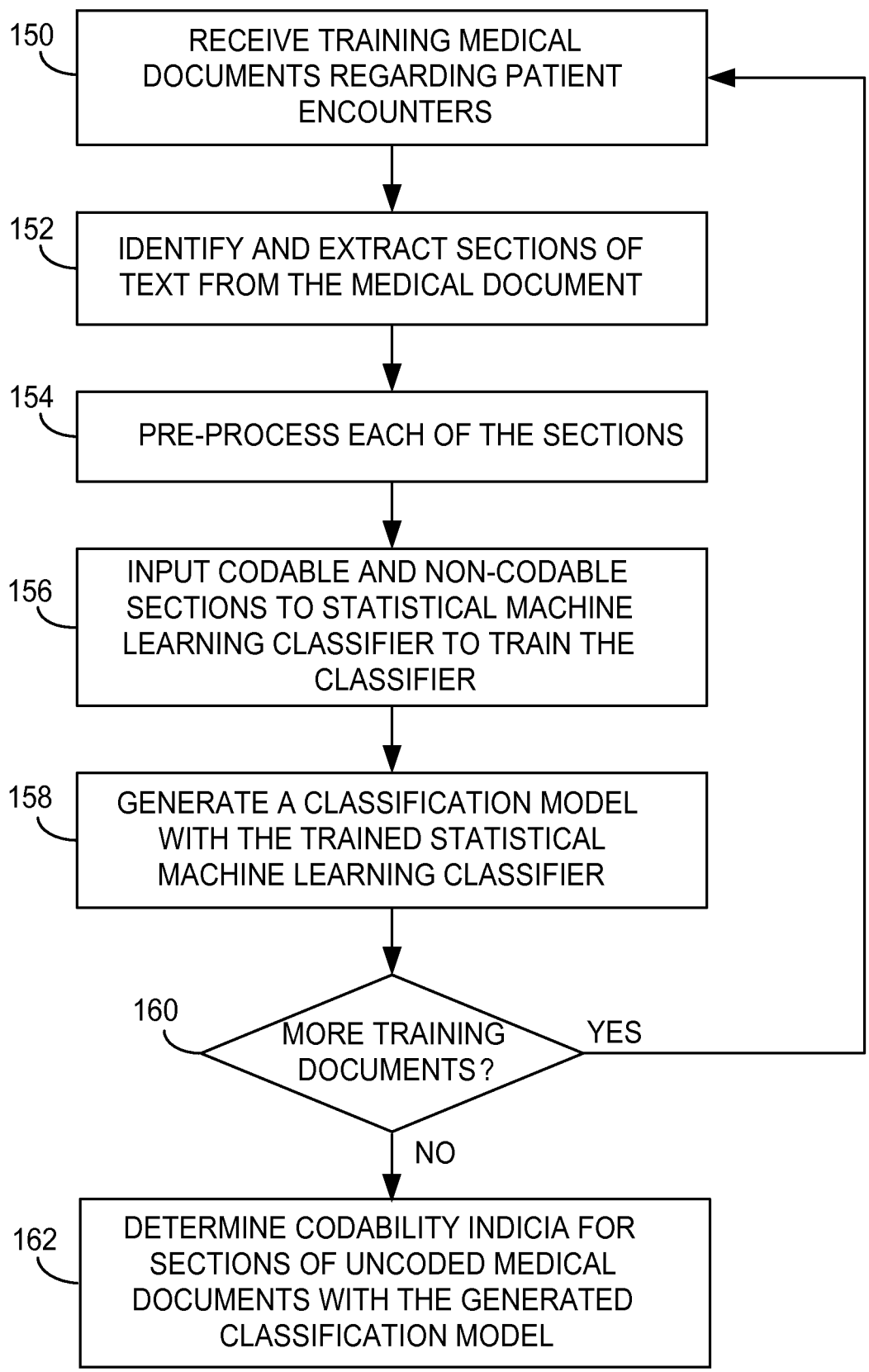
FIG. 4 is a flow diagram illustrating an example technique for generating a classification model with training medical documents.

FIG. 4 is a flow diagram illustrating an example technique for generating a classification model with training medical documents. FIG. 4 will be described from the perspective of sever 22 and repository 24 of FIGS. 1 and 2, although computing device 100 of FIG. 3, any other computing devices or systems, or any combination thereof, may be used in other examples. As shown in FIG. 4, processor 50 may be configured to receive training medical documents regarding respective patient encounters (150). The training medical documents are described as training medical documents in the sense that they are annotated to be used in training a statistical machine learning classifier to identify codable text within sections of the medical documents. These annotations may identify which portions of text contain types of information that are suitable for medical coding and/or those portions of text that do not include information suitable for medical coding. The different types of information identified in the annotations may be associated with respective types of medical coding engines, in some examples.

Processor 50 may then identify and extract sections of text from the medical document (152). Processor 50 may control extraction module 60 to perform this process. In some examples, extraction module 60 may identify the different sections according to a specific formatting break in the text.

In other examples, extraction module 60 may identify different sections according to the instructions contained within the annotations for the respective medical document. Processor 50 may then pre-process each of the sections (154). Pre-processing of each of the sections may prepare the text of the section for training, which may include natural language processing to identify the types of information that are suitable for automated medical coding and those types of information not suitable for automated medical coding.

Processor 50 then inputs the codable and non-codable sections (as identified by the annotations of the training medical documents) to a statistical machine learning classifier to train the classifier to identify (or predict) types of information contained in other medical documents (156). The codable sections (i.e., sections containing information suitable for automated medical coding) may be positive examples of information that are suitable for medical coding. Conversely, the non-codable sections (i.e., sections not containing any information suitable for automated medical coding) may be negative examples of information that are suitable for medical coding. Processor 50 may then generate, or update, a classification model for different types of medical documents with the trained statistical machine learning classifier (158).

If there are more training medical documents available to refine the classification model ("YES" branch of block 160), processor 50 may continue to receive additional training medical documents for updating the classification model (150). In other examples, processor 50 may only generate the classification model once all of the training medical documents have been used to fully train the statistical machine learning classifier. If there are no more training medical documents remaining ("NO" branch of block 160), processor 50 may use generated classification model to determine codability indicia for sections of uncoded medical documents (162).

In some examples, processor 50 may generate a configuration file for medical coding of other medical documents from an entity by application of the classification model to sample medical documents. An entity may typically use several different types of medical documents for a variety of patient encounters and/or different clinician use. As examples, routine preventative exams may use one type of medical documents to describe the patient encounter, each specialist may use a respective type of medical document, and operating room procedures may use another type of medical document. Such types of medical documents may contain the same sections of text that contain similar types of medical information. Therefore, for the same type of medical document, the same types of sections may be associated with the same codability indicia. The configuration file may thus be used to determine codability indicia for sections of new medical documents without processing the text of each section of the new medical documents.

The configuration file may be a table, algorithm, or other set of rules that define the codability indicia for the different sections of a respective type of medical document. In other words, processor 50 can determine codability indicia for sections of medical documents with the generated configuration file instead of applying the classification model to each new section to be processed. The sample medical documents may be non-annotated and uncoded documents from which processor 50 may generate the configuration file. The number of sample medical document used to generate the configuration file may be determined statistically based on the quantity or types of information within the medical documents or the variation in codability indicia that occurs as the configuration file is being generated.

Processor 50 may apply the classification model to each section of the sample medical documents to determine codability indicia. For each type of section processed, processor 50 may maintain a tally, or score, of the determined codability indicia that represents what types of information for which the section is suitable for automated medical coding. For example, different types of codable information may include historical, diagnosis, and procedural information. If processor 50 determines that the same type of section from multiple (e.g., ten, twenty, etc) different sample medical documents is identified as suitable for coding historical information and that same type of section from one other sample medical document is identified as not suitable for coding historical information, processor may determine that the type of section in question is suitable for coding historical information. In other words, processor 50 may select the most common (or more frequent) codability indicia determined for the same types of sections as the codability indicia for that type of section in the configuration file. Some types of sections may be determined to be suitable for automated medical coding of two or more types of information. In other examples, some types of sections may be determined to not have any information suitable for automated medical coding. The configuration file may store these codability indicia for each section of one or more types of medical documents.

Alternatively, processor 50 may determine codability indicia for sections of text by applying the classification model to each section of a newly processed medical document. This approach may be more process intensive that using a configuration file as described above. However, application of the classification model to all text of new medical documents may allow processor 50 to identify information suitable for medical coding in sections that may typically not include information suitable for medical coding and identify sections that do not contain any information suitable for medical coding when those sections may typically contain codable information. Processor 50 may transfer sections of text to appropriate medical coding engines (e.g., one or more coding modules 78) according to the codability indicia determined for each section of the medical documents.

Figure 5:
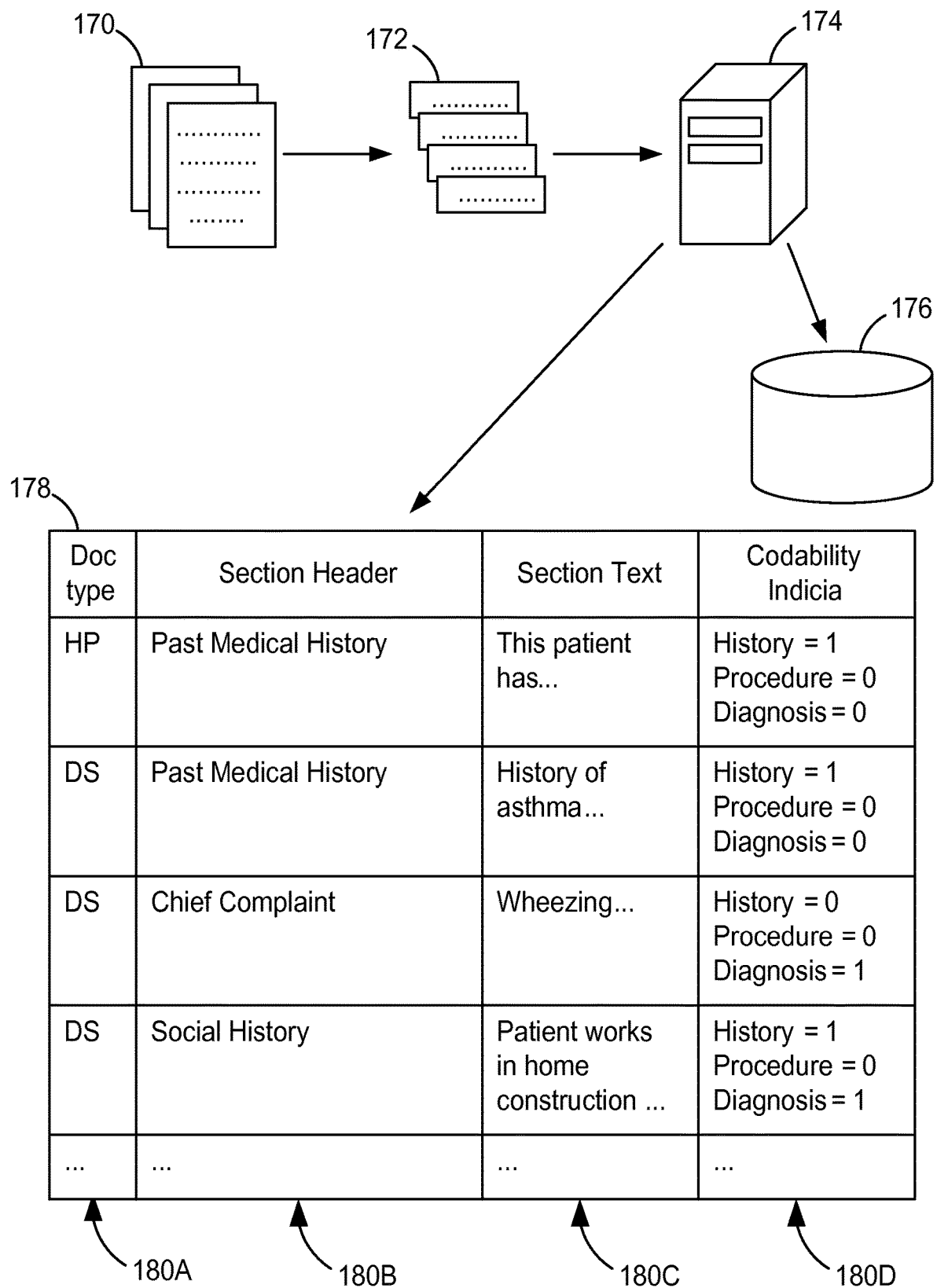
FIG. 5 is an illustration of work flow for determining codability indicia for medical documents to identify the types of medical information within each section of the medical documents.

FIG. 5 is an illustration of work flow for determining codability indicia for medical documents to identify the types of medical information within each section of the medical documents. The work flow of FIG. 5 may be similar to the process described in FIG. 4 related to determining codability indicia. Server 22 may, alone or in combination with another computing device, perform the work flow of FIG. 5. Server 22 may initially receive medical documents 170 from an entity. Medical documents 170 may typically be encoded. Server 22 may identify and extract sections 72 from medical documents 170. Server 22 may also pre-process the text of each of sections 172 to prepare the text for application of the classification model.

Server 22 may then apply classification model 174 to each of sections 172 to determine codability indicia for each of sections 172. Server 22 may output the codability indicia for each of sections 172 to be stored in repository 176 (e.g., an example of repository 24 or another storage device) or for display in chart 178. Chart 178 indicates information related to each section processed by server 22 and the codability indicia determined from the classification model. Chart 178 may be a table, algorithm, software code, or other rules that define the sections and the respective codability indicia.

Chart 178 includes multiple characteristics 180 for each section, such as document type 180A, section header 180B, section text 180C, and codability indicia 180D. Document type 180A may indicate the type of medical document from which the section was extracted. Different types of medical documents may arise from what type of clinician interacted with the patient, the type of patient encounter (e.g., routine exam, specialty examination, or treatment procedure), or a certain facility within a healthcare organization. Each section may include a section header 180B. The section header may indicate the type of information contained within the text following the section header. For example, example section headers may include "Past Medical History," Chief Complaint," and "Social History." Section text 180C may include all or a representative portion of the text contained within each section. In addition, codability indicia 180D represent the types of information for which the section is suitable for automated medical coding.

Codability indicia 180D may include a binary indication of codability for each of one or more types of information. As shown in FIG. 5, codability indicia 180D include three different types of information: "history," "procedure," and "diagnosis." Each of these three types of information may be coded by a respective medical coding engine. Codability indicia 180D may include a binary "1" to indicate that the section includes information that is suitable for automated medical coding of that particular type of information and a binary "0" to indicate that the section does not include information that is suitable for automated medical coding of that particular type of information. For example, for the top "Past Medical History" section, server 22 has determined that the section is suitable for automated medical coding of "history" information and not suitable for automated medical coding of "procedure" or "diagnosis" information. Server 22 may transfer this section of text to a historical coding engine to be coded. As another example, the bottom "Social History" section may have been determined by server 22 to be suitable for automated medical coding of "history" information and "diagnosis" information and not suitable for automated medical coding of "procedure" information. Server 22 may transfer this section of text to both a historical coding engine and a diagnosis coding engine to be coded. In other examples, a section that has codability indicia representing that the section does not have any information suitable for automated medical coding may be skipped or discarded for the coding process.

Codability indicia 180D is shown in FIG. 5 as indications of whether the section is suitable for each type of a plurality of types of automated medical coding. These indications are shown as binary indications. However, codability indicia may be shown in other forms in other examples. Instead of numerical or textual indications of codability, the codability indicia may include one or more colors that represent whether the section includes one or more types of information suitable for automated medical coding. The one or more colors may be selected from a plurality of possible colors corresponding to respective types of information, respective types of coding engines, or even different probabilities that the section is codable. In another example, the codability indicia may include a probability that the section is suitable for automated medical coding or a percentage that the section is suitable for automated medical coding. These indications may represent the best fit of the text of the section to the possible types of information suitable for automated medical coding. Although chart 178 indicates that there are three types of information suitable for automated medical coding, codability indicia may be configured to indicate only whether or not any information is codable, whether two types of information are codable, or whether four or more types of information may be codable.

In some examples, the work flow of FIG. 5 may be performed on sample medical documents to generate a configuration file for different types of medical documents. Server 22 may analyze the codability indicia for each of the same type of section and set the codability indicia of that type of section to the most common codability indicia for that type of section. Server 22 may then use the configuration file to determine the codability indicia for new medical documents. Alternatively, server 22 may use the workflow of FIG. 5 to determine codability indicia for each section of new medical documents and transfer the sections to the corresponding one or medical coding engine.

Figure 6:
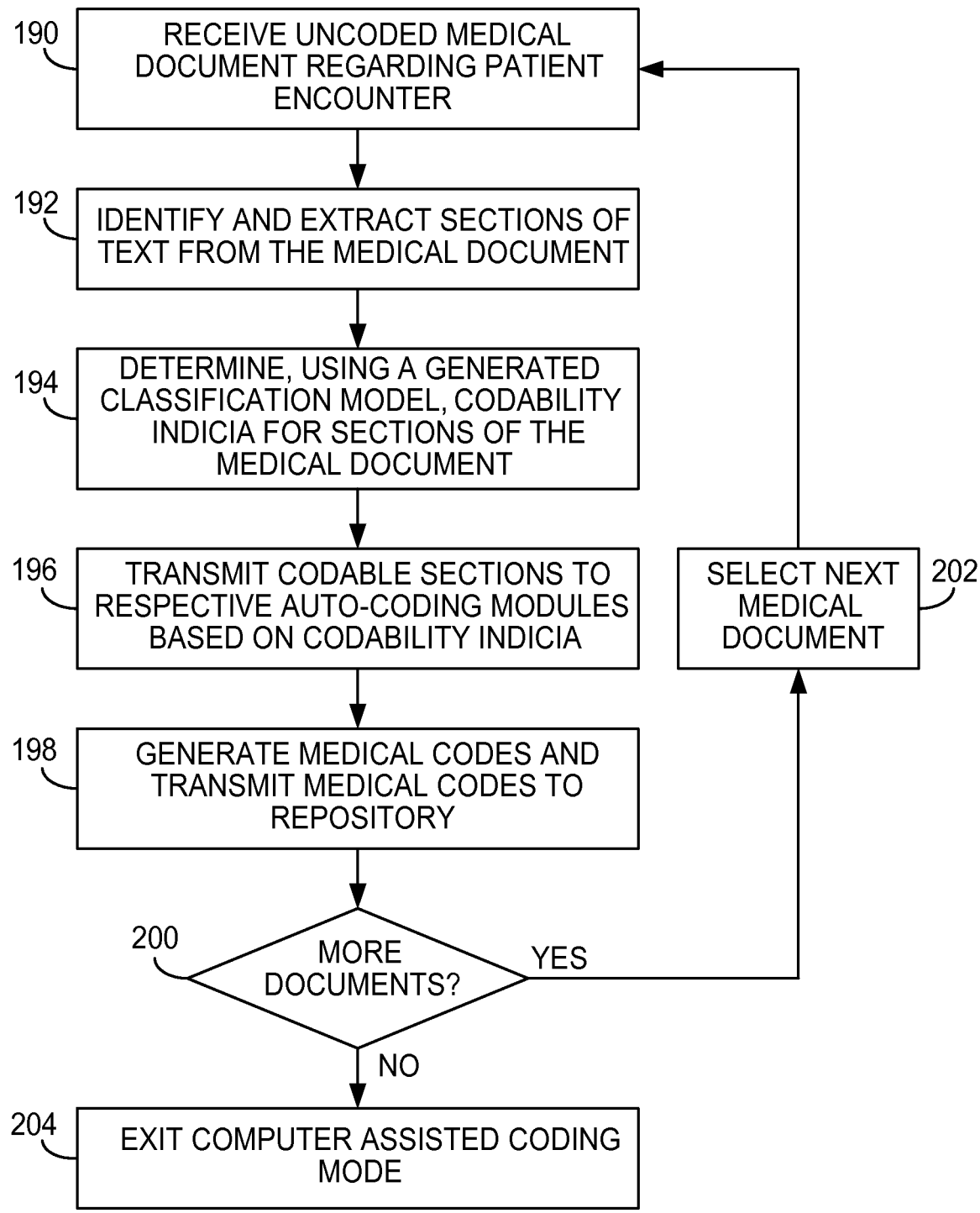
FIG. 6 is a flow diagram illustrating an example technique for determining codability indicia for sections of medical documents and generating medical codes for sections selected based on the respective codability indicia for each section.

FIG. 6 is a flow diagram illustrating an example technique for determining codability indicia for sections of medical documents and generating medical codes for sections selected based on the respective codability indicia for each section. FIG. 6 will be described from the perspective of sever 22 and repository 24 of FIGS. 1 and 2, although computing device 100 of FIG. 3, any other computing devices or systems, or any combination thereof, may be used in other examples. As shown in FIG. 6, processor 50 may be configured to receive an encoded medical document regarding respective patient encounters (190). Processor 50 may then identify and extract sections of text from the medical document (192). Processor 50 may control extraction module 60 to perform this process. In some examples, extraction module 60 may identify the different sections according to a specific formatting break in the text. In other examples, extraction module 60 may identify different sections according to the instructions contained within the annotations for the respective medical document. Processor 50 may also pre-process each of the sections in some examples.

Processor 50 may then determine the codability indicia for each of the extracted sections of the medical document (194). The codability indicia may represent for which types of information each section are suitable for automated medical coding. Processor 50 may then transmit any codable sections of text to the respective automatic medical coding modules or engines (e.g., coding module 76 of FIG. 2) (196). Processor 50 may also skip or otherwise refrain from sending any sections that were determined not suitable for any automated medical coding. Processor 50 may generate medical codes using the appropriate medical coding engine or engines and transmit the medical codes to repository 24 or another computing device (198).

If processor 50 determines that there is another medical document to process ("YES" branch of block 200) processor 50 selects the next medical document (202) and receives the next uncoiled medical document (190). If processor 50 determines that there are no more medical documents for coding ("NO" branch of block 200), processor 50 may exit the computer-assisted coding mode in which processor determines codability indicia and generates medical codes (204). Processor 50 may be one or more processors of server 22 configured to perform the process of FIG. 6. However, one or more additional computing devices may perform one or more of the steps of FIG. 6 in addition to server 22 to create a distributed system.

Figure 7:
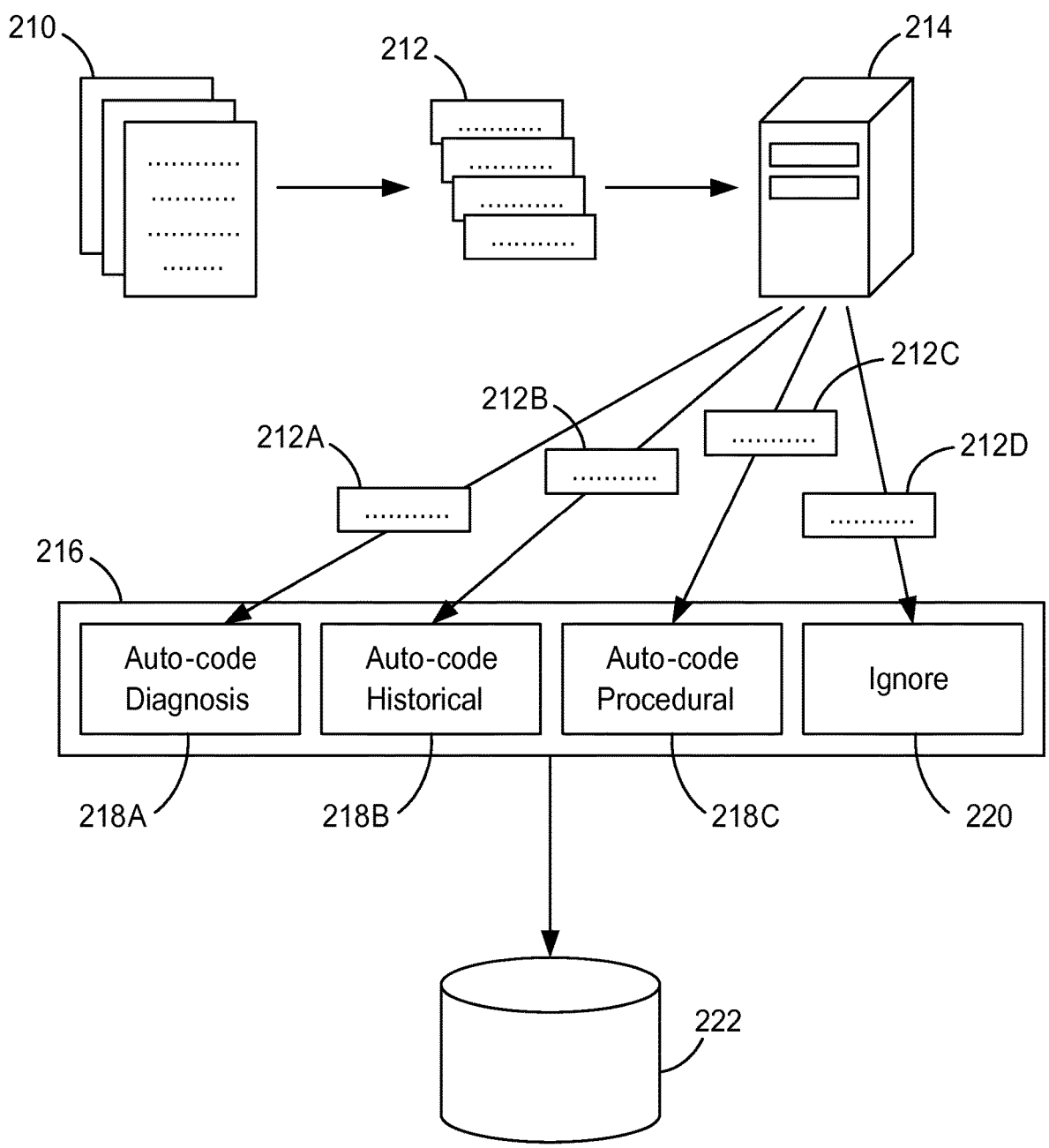
FIG. 7 is an illustration of work flow for distributing sections of medical documents to appropriate medical coding engines based on determined codability indicia for each section.

FIG. 7 is an illustration of work flow for distributing sections of medical documents to appropriate medical coding engines based on determined codability indicia for each section. The work flow of FIG. 7 may be similar to the process described in FIG. 6 related to determining codability indicia and coding sections of text. Server 22 may, alone or in combination with another computing device, perform the work flow of FIG. 7. Server 22 may initially receive medical documents 210 from an entity. Medical documents 210 may typically be uncoded. Server 22 may identify and extract sections 212 from medical documents 210. Server 22 may also pre-process the text of each of sections 212 to prepare the text for application of the classification model in some examples.

Server 22 may then apply classification model 214 to each of sections 212 to determine codability indicia for each of sections 212. As described herein, the codability indicia may represent the types of information contained within the section that is suitable for automated medical coding. These different types of information may be associated with a respective medical coding engine. Server 22 may then transfer sections 212 to the appropriate coding engine or ignore the section if the section is not suitable for automated medical coding.

For example, server 22 may determine different codability indicia for each of sections 212A, 212B, 212C, and 212D (collectively "sections 212") and transfer each of sections 212 to the appropriate coding engines 218A, 218B, 218C (collectively "coding engines 218") or ignore process 220. Coding engines 218 and ignore process 220 may be separate destinations 216 for sections 212. Section 212A may be automatically coded by a diagnosis coding engine 218A, section 212B may be automatically coded by a historical coding engine 218B, and section 212C may be automatically coded by procedural coding engine 218C. In some examples, a section may be coded by multiple different coding engines 218 if the section includes multiple types of information suitable for medical coding. The medical codes generated from coding engines 218 may then be output for storage in repository 222 (e.g., an example of repository 24), for transmission to another computing device, or for display to a user. Since server 22 may determine codability indicia indicating that section 212D may not include any information suitable for medical coding, server 22 may pass section 212D to ignore process 220. In other words, server 22 may not code any information from section 212D. In some examples, server 22 may simply skip section 212D from any coding process instead of transferring section 212D to any location for any additional process. This process of ignoring uncodable sections may streamline the medical coding process by reducing coding engine computations.

The techniques of this disclosure may be implemented in a wide variety of computer devices, such as one or more servers, laptop computers, desktop computers, notebook computers, tablet computers, hand-held computers, smart phones, or any combination thereof. Any components, modules or units have been described to emphasize functional aspects and do not necessarily require realization by one or more different hardware units.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

The techniques described in this disclosure, including those attributed to server 22, repository 24, and/or computing device 100, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, remote servers, remote client devices, or other devices. The term "process" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. For example, any of the techniques or processes described herein may be performed within one device or at least partially distributed amongst two or more devices, such as between server 22 and/or client computing device 12. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A computer-implemented method for processing a medical document, the method comprising:
    receiving, by one or more processors, the medical document, wherein the medical document comprises a plurality of sections for respective types of medical information;
    determining, by the one or more processors, codability indicia for each section of the plurality of sections by automatically comparing text in each section of the plurality of sections to a classification model, wherein the classification model is trained to recognize sections of medical documents that are codable or not codable and the codability indicia represents whether a respective section is configured to be automatically coded by one or more medical coding;

outputting, by the one or more processors, a respective codability indicia for each section of the plurality of sections, wherein sections of the medical document that are identified as not codable are configured to be disregarded or excluded from coding by one or more medical coding engines;

receiving a plurality of training medical documents, each training medical document of the plurality of training medical documents comprises annotations indicating respective sections of the training medical document that are configured to be automatically coded by the one or more medical coding engines;

training a statistical machine learning classifier with the plurality of training medical documents; and generating, with the statistical machine learning classifier, the classification model to determine codability indicia for sections of medical documents, wherein determining the codability indicia for the sections of the medical document comprises determining, by application of the generated classification model to each of the plurality of sections, the codability indicia for each of the sections of the medical document.

2. The method of claim 1, wherein determining codability indicia for each section comprises determining that at least one section of the plurality of sections is configured to not be automatically coded by the one or more medical coding engines.

3. The method of claim 1, wherein determining codability indicia for each section comprises determining that at least one section of the plurality of sections is configured to be automatically coded by the one or more medical coding engines.

4. The method of claim 1, wherein determining codability indicia for each section comprises:
identifying one or more types of medical information contained within the section, the one or more types of medical information selected from a plurality of types of medical information, wherein each type of medical information of the plurality of types of medical information is associated with a respective codability indicium; and
assigning to each section, the one or more codability indicium for the respective types of medical information identified as contained within the respective section.

5. The method of claim 4, wherein the plurality of types of medical information comprises history information, procedural information, diagnostic information, and evaluation management information.

6. The method of claim 1, wherein the codability indicia comprises one or more of a binary indication of whether the section is configured to be automatically coded for each type of a plurality of types of automated medical coding, a probability that the section is configured to be automatically coded by the one or more medical coding engines, a percentage that the section is configured to be automatically coded by the one or more medical coding engines, and respective colors selected from a plurality of colors that indicate whether the section is configured to be automatically coded by the one or more medical coding engines.

7. The method of claim 1, further comprising:
identifying each of the plurality of sections in the medical document; and
extracting the plurality of sections for individual analysis by the classification model.

8. The method of claim 7, wherein identifying each of the plurality of sections comprises separating portions of text within the medical document according to one or more formatting breaks located within the text.

9. The method of claim 8, wherein the one or more formatting breaks comprise one or more headers located within the text, and wherein each of the one or more headers corresponds to a respective section of the plurality of sections.

10. The method of claim 1, further comprising presenting, on a display, the codability indicia for one or more sections of the plurality of sections.

11. The method of claim 1, wherein the medical document has not been subjected to the automated medical coding prior to the determination.

12. The method of claim 1, further comprising:
selecting, based on the determined codability indicia, one or more sections of the plurality of sections to be automatically coded by the one or more medical coding engines;
generating, via application of a medical coding engine to each of the one or more sections, one or more medical codes for the one or more selected sections; and
outputting the one or more medical codes for the one or more selected sections.

13. The method of claim 1, wherein each section of the plurality of sections corresponds to one or more types of a plurality of types of sections, and wherein the method further comprises:
determining, for each type of the plurality of types of sections and based on the determined codability indicia for each section, codability indicia for each type of the plurality of types of sections; and
generating a configuration file identifying the codability indicia for each type of the plurality of types of sections, wherein codability indicia are determined for new sections according to the configuration file.

14. A computerized system for processing a medical document, the system comprising:
a memory; and
one or more processors configured to:
receive the medical document and store the medical document in the memory, wherein the medical document comprises a plurality of sections for respective types of medical information;
determine codability indicia for each section of the plurality of sections by automatically comparing text in each section of the plurality of sections to a classification model, wherein the classification model is trained to recognize sections of medical documents that are codable or not codable and the codability indicia represents whether a respective section is configured to be automatically coded by one or more medical coding engines;
output a respective codability indicia for each section of the plurality of sections, wherein sections of the medical document that are identified as not codable are configured to be disregarded or excluded from coding by the one or more medical coding engines;
receive a plurality of training medical documents, each training medical document of the plurality of training medical documents comprises annotations indicating respective sections of the training medical document that are configured to be automatically coded by the one or more medical coding engines;

train a statistical machine learning classifier with the plurality of training medical documents; and generate, with the statistical machine learning classifier, the classification model to determine codability indicia for sections of medical documents, wherein determining the codability indicia for the sections of the medical document comprises determining, by application of the generated classification model to each of the plurality of sections, the codability indicia for each of the sections of the medical document.

15. The system of claim 14, wherein the one or more processors are configured to determine codability indicia for each section by determining that at least one section of the plurality of sections is not configured to be automatically coded by the one or more medical coding engines.

16. The system of claim 14, wherein the one or more processors arc configured to determine codability indicia for each section by:

identifying one or more types of medical information contained within the section, the one or more types of medical information selected from a plurality of types of medical information, wherein each type of medical information of the plurality of types of medical information is associated with a respective codability indicium; and assigning, to each section, the one or more codability indicium for the respective types of medical information identified as contained within the respective section.

17. The system of claim 14, wherein the codability indicia comprises one or more of a binary indication of whether the section is not configured to be automatically coded for each type of a plurality of types of automated medical coding, a probability that the section is configured to be automatically coded by the one or more medical coding engines, a percentage that the section is configured to be automatically coded by the one or more medical coding engines, and respective colors selected from a plurality of colors that indicate whether the section is configured to be automatically coded by the one or more medical coding engines.

18. The system of claim 14, wherein the one or more processors are configured to:

identify each of the plurality of sections in the medical document according to one or more formatting breaks within the text; and extract the plurality of sections for individual analysis by the classification model.

19. The system of claim 14, wherein the one or more computing devices are further configured to control a display to present the codability indicia for the one or more sections of the plurality of sections.

20. The system of claim 14, wherein the medical document has not been subjected to the automated medical coding prior to the determination.

21. The system of claim 14, wherein the one or more computing devices are further configured to:

select, based on the determined codability indicia, one or more sections of the plurality of sections is configured to be automatically coded by the one or more medical coding engines;

generate, via application of a medical coding engine to each of the one or more sections, one or more medical codes for the one or more selected sections; and output the one or more medical codes for the one or more selected sections.

22. A non-transitory computer-readable storage medium comprising instructions that, when executed, cause one or more processors to:

receive the medical document wherein the medical document comprises a plurality of sections for respective types of medical information;

determine codability indicia for each section of the plurality of sections by automatically comparing text in each section of the plurality of sections to a classification model, wherein the classification model is trained to recognize sections of medical documents that are codable or not codable and the codability indicia represents whether a respective section is configured to be automatically coded by one or more medical coding engines;

output a respective codability indicia for each section of the plurality of sections, wherein sections of the medical document that are identified as not codable are configured to be disregarded or excluded from coding by the one or more medical coding engines;

receive a plurality of training medical documents, each training medical document of the plurality of training medical documents comprises annotations indicating respective sections of the training medical document that are configured to be automatically coded by the one or more medical coding engines;

train a statistical machine learning classifier with the plurality of training medical documents; and generate, with the statistical machine learning classifier, the classification model to determine codability indicia for sections of medical documents, wherein determining the codability indicia for the sections of the medical document comprises determining, by application of the generated classification model to each of the plurality of sections, the codability indicia for each of the sections of the medical document.

23. The computer-readable storage medium of claim 22, wherein the instructions that, when executed, cause the one or more processors to determine codability indicia for each section comprise instructions that, when executed, cause the one or more processors to determine that at least one section of the plurality of sections is configured to not be automatically coded by the one or more medical coding engines.

24. The computer-readable storage medium of claim 22, wherein the instructions that, when executed, cause the one or more processors to determine codability indicia for each section comprise instructions that, when executed, cause the one or more processors to:

identify one or more types of medical information contained within the section, the one or more types of medical information selected from a plurality of types of medical information, wherein each type of medical information of the plurality of types of medical information is associated with a respective codability indicium; and assign, to each section the one or more codability indicium for the respective types of medical information identified as contained within the respective section.

25. The computer readable storage medium of claim 22, further comprising instructions that cause the one or more processors to:

select, based on the determined codability indicia, one or more sections of the plurality of sections are not configured to be automatically coded by the one or more medical coding engines;

generate, via application of a medical coding engine to each of the one or more sections, one or more medical codes for the one or more selected sections; and output the one or more medical codes for the one or more selected sections.

\* \* \* \* \*